United States Patent [19]

Coulter et al.

[11] 4,009,443
[45] * Feb. 22, 1977

[54] METHOD AND APPARATUS FOR PROVIDING PRIMARY COINCIDENCE CORRECTION DURING PARTICLE ANALYSIS UTILIZING TIME GENERATION TECHNIQUES

[75] Inventors: Wallace H. Coulter, Miami Springs; Walter R. Hogg, Miami Lakes; Millard D. Longman, Jr.; Stephen Campbell, both of Hialeah; Edward Neal Doty, Pompano, all of Fla.

[73] Assignee: Coulter Electronics, Inc., Hialeah, Fla.

[ * ] Notice: The portion of the term of this patent subsequent to Feb. 3, 1993, has been disclaimed.

[22] Filed: Apr. 3, 1975

[21] Appl. No.: 564,722

Related U.S. Application Data

[63] Continuation-in-part of Ser. No. 485,160, July 2, 1974, Pat. No. 3,936,741, which is a continuation of Ser. No. 407,235, Oct. 17, 1973, abandoned.

[52] U.S. Cl. .................. 328/111; 235/92 PC; 307/234; 324/71 CP; 328/115
[51] Int. Cl.[2] ................ H03K 5/20; G01N 27/00
[58] Field of Search .......... 328/111, 112, 115–117; 307/234; 324/71 CP; 235/92 PC

[56] References Cited

UNITED STATES PATENTS

| | | | |
|---|---|---|---|
| 3,171,892 | 3/1965 | Pantle | 328/111 |
| 3,600,688 | 8/1971 | Booth | 328/111 |
| 3,611,157 | 10/1971 | Hughes | 328/112 |

Primary Examiner—Stanley D. Miller, Jr.
Attorney, Agent, or Firm—Silverman & Cass, Ltd.

[57] ABSTRACT

A method and apparatus for correcting a particle pulse count subject to coincidence error is disclosed wherein particle pulses, developed in response to passage of particles in a particulate system through a sensing zone, are counted for a predetermined period of time. The predetermined period of time is increased or extended in response to each pulse counted by a time increment that is related to a characteristic of the counted pulse, such as the pulse width, duration, or amplitude. The total additional time period allows the counting of additional particle pulses such that the total count at the end of the extended time period is an error corrected count for the number of particles detected in the predetermined time period.

21 Claims, 6 Drawing Figures

METHOD AND APPARATUS FOR PROVIDING PRIMARY COINCIDENCE CORRECTION DURING PARTICLE ANALYSIS UTILIZING TIME GENERATION TECHNIQUES

CROSS REFERENCE TO RELATED APPLICATIONS

This application is a continuation-in-part of copending U.S. patent application Ser. No. 485,160, now U.S. Pat. No. 3,936,741, filed July 2, 1974 which is a continuation of U.S. patent application Ser. No. 407,235, now abandoned, filed Oct. 17, 1973. The continuation-in-part, continuation and parent applications all are assigned to the same assignee.

BACKGROUND OF THE INVENTION

This invention is directed to particle counting methods and apparatuses which provide a time correction to the time period particle pulses are counted so that coincidence phenomena resulting in fewer particle pulses being counted in a predetermined time period does not induce an error in the particle pulse count ultimately obtained. The particle counting methods and apparatuses concerned employ particle sensing zones wherein the presence of one particle within the zone masks or hides the presence of another particle which also may be within the sensing zone. This invention particularly is directed to, but not limited to, the correct determination of non-electrical properties, such as size and count of microscopic particles by measuring electrical properties (Patent Office Class 324-71NE).

Now well known in the art of electronic particle counting and analyzing is apparatus marketed primarily under the trademark "Coulter Counter," and owned by the assignee of this application. Such apparatus and portions thereof are disclosed in several U.S. patents, for example U.S. Pat. Nos. 2,656,508; 2,985,830; and 3,259,842 (class 324-71). A significantly important portion of such Coulter type of apparatus is the minute scanning aperture or scanning ambit or sensing zone relative to or through which pass and are detected and counted, single particles at a rate often well in excess of one thousand per second. Because of the physical parameters of the scanning aperture, and particle concentration, coincidence of two particles in the scanning ambit occurs quite often.

It has been found that once a particle pulse produced by the presence of a particle in the scanning ambit, exceeds the threshold setting of the apparatus and is detected, no other pulse will be produced in response to other particles in the scanning ambit until such time as the particles have cleared the sensing zone. As the presence of a first particle masks a second particle causing a coincidence error, the coincidence error is a function of the time that detected particles are in the scanning ambit, and the total coincidence error is a function of the total time that particles are in the scanning aperture during the detecting and counting process. Since the coincidence error is a function of the time that each particle is in the scanning aperture, it can also be said that the coincidence error is a function of the duration of each particle pulse produced and detected in response to passage of a particle through the scanning ambit. It has also been found that the coincidence error is functionally related to the rate at which particles pass through the scanning ambit and, therefore, the particle pulse repetition rate if this rate is determined only by particle concentration.

SUMMARY OF THE INVENTION

In practicing this invention an apparatus is provided for automatically correcting a particle pulse count subject to coincidence error wherein particle pulses are developed in response to passage of particles in a particulate system through a particle sensing device. The apparatus includes a timer which is operative to count particle pulses received for a predetermined period of time. A control device is coupled to the timer and is operative to increase the predetermined period of time by a time increment in response to each particle pulse. The duration of the time increment is related to particular characteristics of each particle pulse, for example the pulse duration or amplitude.

In one embodiment of this invention, a second time increment is added to the predetermined period of time in response to each particle pulse. This second time increment may be either a fixed duration or a duration which is proportional to the repetition rate of the particle pulses received.

The method for correcting a particle pulse count subject to a coincidence error is also envisioned as being within the scope of this invention. This method includes the steps of a. countisng the particle pulses received for a predetermined period of time, and b. increasing the predetermined period of time by a time increment that is related to particular characteristics of each pulse counted such as, for example the pulse width.

DETAILED DESCRIPTION OF THE DRAWINGS

Figure 1:
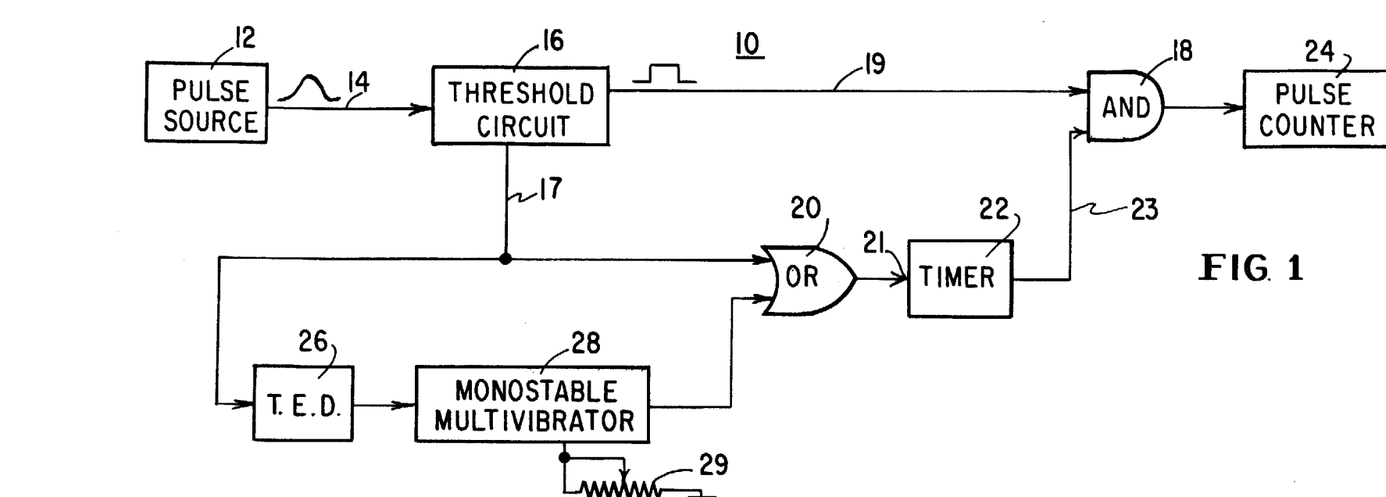
FIG. 1 is a block diagram of an apparatus embodying the features of this invention.

Referring to FIG. 1 there is shown an apparatus embodying the invention and identified generally by the reference number 10. A pulse source 12 can be the aperture tube and related circuitry of a Coulter type particle detector such as is shown and described in U.S. Pat. Nos. 2,656,508 and 3,259,842, wherein particle pulses are developed in response to the passage of particles in a particulate system through the sensing zone of the aperture tube. The particle pulses developed by the pulse source 12 are coupled via conductor 14 to a threshold circuit 16. Pulses such as appear on conductor 14 are shown in Graph A of FIG. 3, and are identified as pulses 44, 46, 48 and 50.

Figure 3:
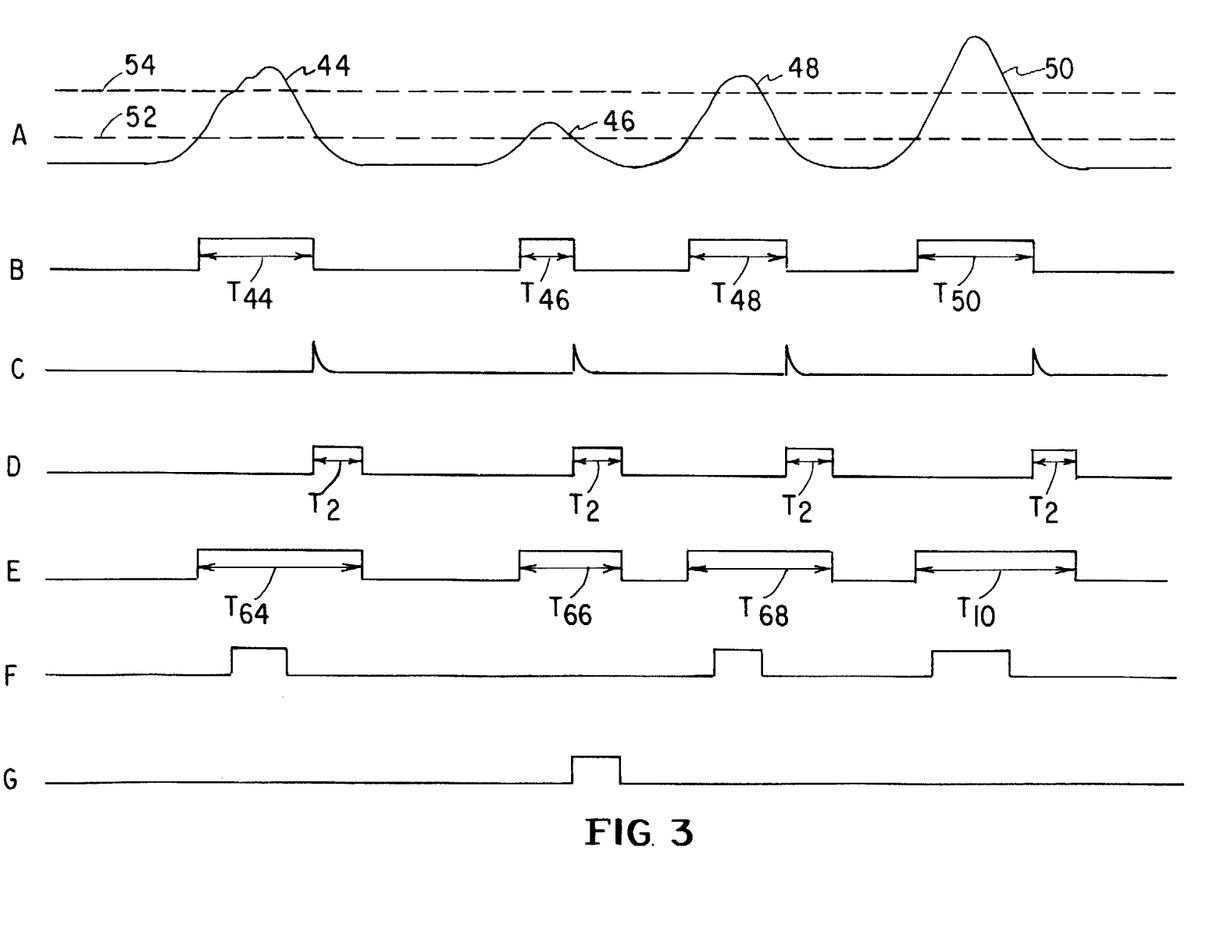
FIG. 3 is a graph of curves representative of signals at various points of the apparatus shown in FIGS. 1 and 2.

Threshold circuit 16 has a low threshold level. This low threshold level is represented by the dashed line 52 in Graph A of FIG. 3. When the low threshold level 52 is exceeded by a particle pulse from pulse source 12, threshold circuit 16 develops a threshold pulse having a fixed amplitude and duration which is equal to the period that the particular pulse exceeds the threshold level. Graph B of FIG. 3 shows the threshold pulses developed in response to particle pulses 44, 46, 48 and 50. The periods of these pulses are $T_{44}$, $T_{46}$, $T_{48}$ and $T_{50}$, respectively. The threshold pulses shown in Graph B are developed at conductors 17 and 19 in FIG. 1. Conductor 19 couples the threshold pulses to one input of an AND gate 18.

Timer 22 is of the type commonly known in the art which when enabled via a push-button or a start signal associated with the start of the operation of the pulse source 12 will develop an output signal at conductor 23 for a fixed period of time. That is, timer 22 once initiated, will measure a predetermined time interval of, for example 5 seconds and, during that predetermined time interval, it will develop an output or timer signal at conductor 23. The timer signal developed by timer 22 is coupled via conductor 23 to the second input of AND gate 18 for the predetermined time interval or period of operation of timer 22, thus partially enabling AND gate 18. AND gate 18 will be fully enabled during the predetermined time period by receipt of a threshold pulse on conductor 19 such as, for example those pulses shown in Graph B of FIG. 3. When AND gate 18 is fully enabled it will develop an AND gate output pulse which is coupled to pulse counter 24. Pulse counter 24 will count the pulse coupled from AND gate 18. As AND gate 18 develops its AND gate signal during the predetermined time period in response to the threshold pulses, which are developed in response to the particle pulses in excess of the threshold level, pulse counter 24 will be counting each particle pulse in excess of the threshold level during the predetermined time period.

Conductor 17 couples the threshold pulses developed by threshold circuit 16 to one input of an OR gate 20, and to the input of a trailing edge detector circuit (TED) 26. Trailing edge detector circuit 26 is operative in response to the trailing edge of each one of the threshold pulses received to develop a pulse. Pulses developed in response to threshold pulses $T_{44}$, $T_{46}$, $T_{48}$ and $T_{50}$ are shown in Graph C of FIG. 3. The pulses developed by trailing edge detector circuit 26 are coupled to the input of a monostable multivibrator 28, commonly known in the art as a one shot. Monostable multivibrator 28 will develop an output pulse of fixed amplitude and predetermined duration in response to each pulse coupled to its input from trailing edge detector circuit 26. The duration of the pulse developed by monostable multivibrator 28 may be varied by adjusting the potentiometer 29 shown as being coupled to monostable multivibrator 28. The pulses of fixed amplitude and predetermined duration, developed by monostable multivibrator 28 in response to threshold pulses $T_{44}$, $T_{46}$, $T_{48}$ and $T_{50}$ are shown in Graph D of FIG. 3. They are shown as having a fixed duration identified as $T_2$. These pulses are coupled from monostable multivibrator 28 to a second input of OR gate 20.

OR gate 20 develops an output pulse in response to an input pulse at either one of the two inputs. The output or OR gate pulse will be present for the full duration of the input pulse at either one of the two inputs. Accordingly, OR gate 20 will develop an OR gate pulse for the full duration of each threshold pulse. Because the threshold pulse is coupled to one input of OR gate 20 via conductor 17, and the monostable pulse is coupled from monostable multivibrator 28 to the second input of OR gate 20, immediately upon the termination of a threshold pulse, OR gate 20 will maintain the OR gate pulse for a fixed increment or period $T_2$. Graph E of figure represents the output of OR gate 20 in response to particle pulses 44, 46, 48 and 50. It can be seen that the pulse identified as having a period $T_{64}$ is equal to the period of threshold pulse $T_{44}$ and $T_2$. Similarly, the pulses identified as $T_{66}$, $T_{68}$, and $T_{70}$ correspond in duration to the period of the corresponding threshold pulse plus a fixed period $T_2$.

Timer 22 also includes an inhibit circuit such that when a signal is coupled to inhibit input 21 of timer circuit 22 measurement or counting of the predetermined time period will be inhibited. The measurement or counting of the predetermined time period will be inhibited for the duration of the signal coupled to inhibit input 21. The OR gate signals developed at output of OR gate 20 are coupled to the inhibit input 21 of timer 22 inhibiting the measuring or counting of the predetermined time period for the duration of the OR gate signals.

The circuitry coupling threshold circuit 16 to the inhibit input 21 of timer 22 acts as previously noted to inhibit the operation of timer 22 for particular time increments in response to each particle pulse received and detected. A portion of each particular time increment is a function of the duration of each particle pulse received in excess of the threshold level. Another portion of the time increment is of fixed duration in response to each particle pulse received and detected. These time increments extend the total time period counted or measured by timer 22 so that particle pulses may be counted for a time period greater than the predetermined time period originally selected. This additional time period counted, and resulting from these time increments, and the particle pulses detected and counted during this additional time period, provide an error correction to the particle pulse count obtained during the predetermined time period such that the total particle pulse count will be an error corrected particle pulse count for the predetermined time period.

Figure 2:
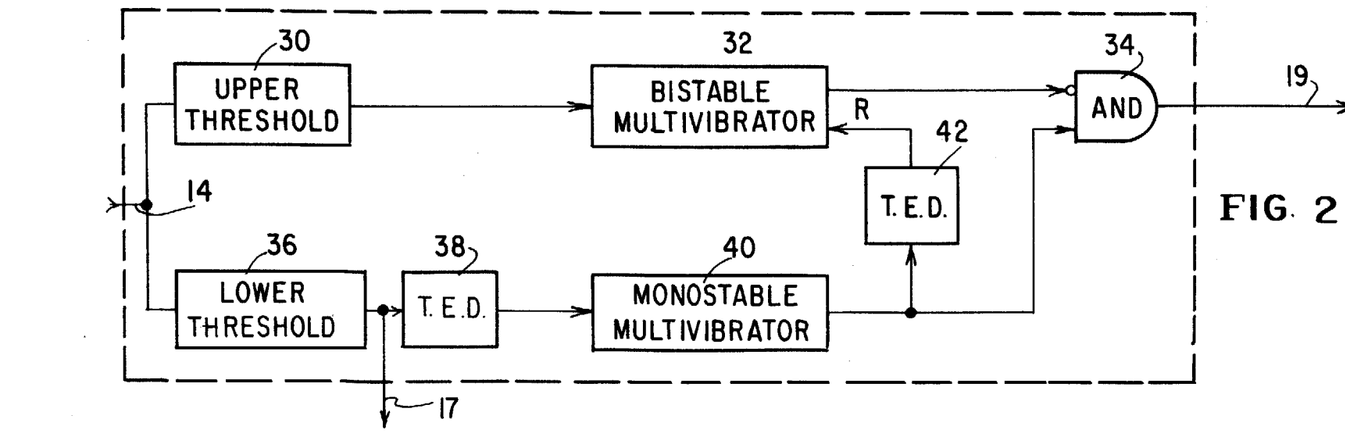
FIG. 2 is a block diagram of a threshold circuit which may be used in the apparatus shown in FIG. 1.

Although the threshold circuit 16 is shown and described in FIG. 1 as a single, low level threshold circuit, it is to be understood that other types of threshold circuits may be employed in the apparatus shown in FIG. 1. For example, a "window" type threshold circuit may be employed wherein pulses only falling within a particular amplitude range are detected and produce threshold pulses at conductor 19. The operation of a "window" type threshold circuit is shown and described in U.S. Pat. No. 3,259,842. FIG. 2 shows an embodiment of a "window" type threshold circuit for use in the apparatus of FIG. 1.

Referring to FIG. 2, each particle pulse from pulse source 12 in FIG. 1 is coupled via conductor 14 to an upper threshold 30 and a lower threshold 36. For purposes of the description of the operation of this "window" threshold circuit the particle pulses shown in Graph A of FIG. 3 will be assumed to be coupled via conductor 14 to upper and lower thresholds 30 and 36 respectively. Referring to Graph A, the lower threshold level is represented by the dashed line 52 and the upper threshold level is represented by the dashed line 54. If a particle pulse exceeds the lower threshold level 52 of lower threshold 36, a threshold pulse will be developed by lower threshold 36 and coupled to conductor 17. Pulse $T_{44}$ in Graph B represents the output threshold pulse at conductor 17 for particle pulse 44 when threshold level 52 of lower threshold 36 is exceeded. If the particle pulse coupled to upper threshold 30 exceeds the upper threshold level 54, upper threshold 30 will develop an output pulse which is coupled to a bistable multivibrator 32. Graph F of FIG. 3 shows the output of upper threshold 30 during the period that particle pulses 44, 48 and 50 in Graph A exceed upper threshold level 54.

The pulse developed by upper threshold 30 and coupled to bistable multivibrator 32 causes bistable multivibrator 32 to change states and develop an output pulse. This output pulse is coupled via an inverted input to AND gate 34. The inverted input acts to transform AND gate 34 to a veto type AND gate. As a consequence, when bistable multivibrator 32 develops an output signal, that is, when upper threshold 30 is activated in response to a pulse which exceeds the upper threshold level 54, AND gate 34 will be inhibited from developing an output signal at conductor 19. Because of this inhibit when the upper threshold is exceeded, indicating that the particle pulse amplitude is outside of the window, a pulse will not be coupled to AND gate 18 for counting by pulse counter 24.

Each pulse developed by lower threshold 36 such as for example, pulse $T_{44}$ shown in Graph B is also coupled to a trailing edge detector (TED) 38. Trailing edge detector 38 will develop a pulse in response to the trailing or terminating edge of the threshold pulse. Graph C shows the pulse developed by trailing edge detector circuit 38 in response to $T_{44}$. The pulse developed by trailing edge detector circuit 38 is coupled to a monostable multivibrator 40 which, in the embodiment shown, can be identical to monostable multivibrator 28 and have the same time period, so that the pulses shown in Graph D of FIG. 3 could equally as well represent the pulses developed by monostable multivibrator 40 as the pulses represented by the monostable multivibrator 28. Monostable multivibrator 40 develops a pulse of fixed amplitude and predetermined duration in response to the pulse from trailing edge detector 38. This pulse is represented in FIG. 3, Graph D. The pulse developed by monostable multivibrator 40 is coupled to a second trailing edge detector 42 and to a second input of AND gate 34. When AND gate 34 is not inhibited, that is, when the upper threshold level 54 is not exceeded, the pulse coupled from monostable multivibrator 40 will cause AND gate 34 to develop an AND gate signal at output 19. When AND gate 34 is inhibited via an output signal from bistable multivibrator 32, it will not develop an AND gate signal at conductor 19 in response to a pulse from monostable multivibrator 40. In Graph A of FIG. 3 it can be seen that particle pulses 44, 48 and 50 exceed the low threshold level 52 of the low threshold 36 and the upper threshold level 54 of upper threshold 30. Particle pulse 46 exceeds the lower threshold level 52 of lower threshold 36 and does not exceed upper threshold level 54 of upper threshold 30. Consequently only particle pulse 46 is within the window. Referring now to Graph G of FIG. 3, it can be seen that the output of veto AND gate 34, represented in Graph G only develops an output signal after particle pulse 46.

Trailing edge detector 42, coupled to the output of monostable multivibrator 40 acts in response to the trailing edge of the monostable multivibrator pulses as represented in Graph D of FIG. 3 to develop pulses which are coupled to the reset input of bistable multivibrator 32. These pulses act to reset bistable multivibrator 32 and terminate its output signal such that AND gate 34 is no longer inhibited from responding to a pulse at its second input. This resetting of bistable multivibrator 32 is necessary in order to allow threshold circuit 16 to respond to the next particle pulse in the particle pulse train.

It should be noted for purposes of this application that when a "window" type threshold circuit 16 is employed, the output coupled to conductor 19 is not the same as the output coupled to conductor 17. The output coupled to conductor 19 is a count output which is ultimately coupled to pulse counter 24 in FIG. 1 in order to count the number of pulses falling within the "window" of threshold circuit 16. However, all pulses in excess of the lower threshold level 52 of low threshold 36 in threshold circuit 16 must be considered in determining the amount of error correction time to be added to the time period measured by timer 22. For this reason, the output of threshold circuit 16 is coupled to conductor 17 which couples any and all pulses in excess of the lower threshold level 52 to the error correction circuitry in FIG. 1 consisting of OR gate 20, negative trailing edge detector 26 and monostable multivibrator 28. All of these pulses are employed, therefore, for developing the OR gate signal coupled from OR gate 20 to the inhibit input 21 of timer 22.

Figure 4:
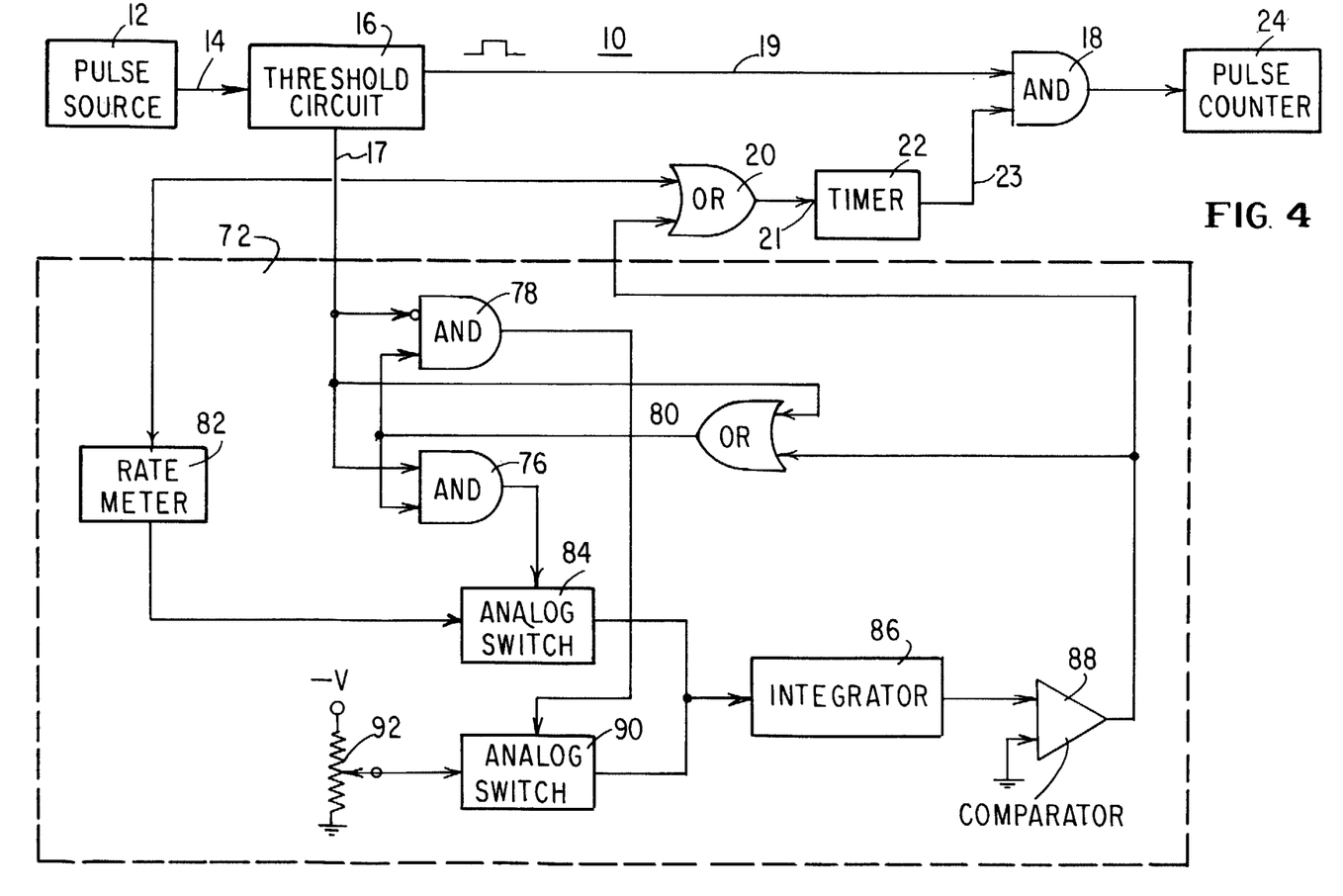
FIG. 4 is a block diagram of another embodiment of the apparatus of this invention.

As previously noted, negative trailing edge detector 26 and monostable multivibrator 28 in the embodiment of FIG. 1 form a circuit which inhibits operation of timer 22 for a fixed or predetermined period of time in response to each particle pulse detected. It has been found that the error correction can be enhanced if timer 22 is inhibited for a second time increment whose duration is a function of the rate of detection of the particle pulses rather than a fixed time increment. FIG. 4 is a block diagram of an apparatus including circuitry for inhibiting operation of timer 22 by a period which is proportional to the rate of detection of particle pulses. As all other portions of the apparatus shown in FIG. 4 are identical to the apparatus shown in FIG. 1, these identical portions, which are identically numbered, will not be described. The operation of these portions as they are identical to that described with respect to FIG. 1 also will not be repeated. Only the operation of the circuitry which inhibits timer 22 for a time period which is a function of the repetition rate of the detected particle pulses will be described.

The threshold pulses developed at conductor 17 by threshold circuit 16 in the embodiment of FIG. 4 are coupled to an inverted input of AND gate 78, one input of an OR gate 80, one input of an AND gate 76, and rate meter 82. Rate meter 82 can be the type such as is described in U.S. Pat. No. 3,757,213. It will develop a DC voltage whose amplitude is a function of the repetition rate of the threshold pulses coupled thereto. The DC voltage developed by rate meter 82 is coupled to one input of an electronic or analog switch 84. Details of an electronic switch which may be employed are also shown in Pat. No. 3,757,213.

Inverting one input of AND gate 78 makes AND gate 78 a veto AND gate. Consequently, whenever a threshold pulse is coupled to the inverted input via conductor 17, AND gate 78 will be inhibited from developing an AND gate signal at its output. The threshold pulses coupled via conductor 17 to the input of OR gate 80 causes OR gate 80 to develop an OR gate signal at its output which is coupled to a second input of AND gates 76 and 78. As AND gate 78 is inhibited, it will not develop an AND gate signal. As the first input to ANd gate 76 is coupled to threshold circuit 16 via conductor 17, the presence of a threshold pulse on conductor 17 and the OR gate signal at its second input will cause AND gate 76 to change states and develop an AND gate signal at its output. The AND gate signal is coupled from AND gate 76 to the control input of analog switch 84, opening analog switch 84 and allowing the DC voltage developed by rate meter 82 to be coupled to integrator 86. Integrator 86 will integrate this DC voltage for the period that the threshold pulse is present at conductor 17 and develop an integration voltage. The integration voltage developed by integrator 86 is coupled to one input of comparator 88. The second input of comparator 88 in this embodiment is coupled to a ground or reference potential. Consequently, when the integration voltage developed by integrator 86 exceeds zero or reference potential, comparator 88 will develop an output signal which is coupled to a second input of OR gate 80 and to the second input of OR gate 20. This comparator output signal will cause OR gate 20 to develop an OR gate signal at its output which is coupled to the inhibit terminal 21 of timer 22 inhibiting the measurement or counting of timer 22.

The comparator output signal developed by comparator 88 and coupled to the input of OR gate 80 causes OR gate 80 to maintain its OR gate signal at the second input of AND gates 76 and 78 after the termination of the threshold pulse developed at conductor 17. Upon the termination of the threshold pulse developed at conductor 17, the inverted input of AND gate 78 will no longer inhibit the operation of veto AND gate 78. With an OR gate signal coupled to the second input of AND gate 78, AND gate 78 will change states and develop an AND gate signal at its output which is coupled to the control input of analog switch 90. Analog switch 90 is coupled via a potentiometer 92 to negative supply potential. Upon receipt of the AND gate signal from veto AND gate 78 analog switch 90 will couple the negative potential from potentiometer 92 to integrator 86. Integrator 86 will begin integrating this negative voltage causing the integration voltage developed at its output to decrease towards zero or reference potential. When zero or reference potential is reached, comparator 88 will change states and terminate its comparator output signal. When the comparator output signal is terminated, OR gates 20 and 80 will no longer develop an OR gate signal at their outputs, so that veto AND gate 78 will no longer develop an AND gate signal at its output and timer 22 will no longer be inhibited from counting or measuring the predetermined time.

In certain types of particulate systems, the range of particulate size is well defined. For example, in the counting and analysis of blood, three discrete size ranges are present, one for red cells, a second for white cells and a third for platelets. In such systems, the cell dimensions generally are small as compared to the dimensions of the scanning aperture. Consequently, the width of the pulse obtained by passage of a cell through the scanning aperture is dependent upon the geometry of the aperture itself and the flow rate of the fluid through the aperture and not on the cell size. The pulses developed in such systems, for example, the pulses for red blood cells, all have substantially the same width. Stated differently, because of the aperture geometry and fluid flow rate the time period of any cell within the scanning aperture is generally constant for the system. The coincidence error is a function of this constant time period as is the resulting constant pulse width. In such systems the entire circuit shown in FIGS. 1 and 4 is unnecessary.

Figure 5:
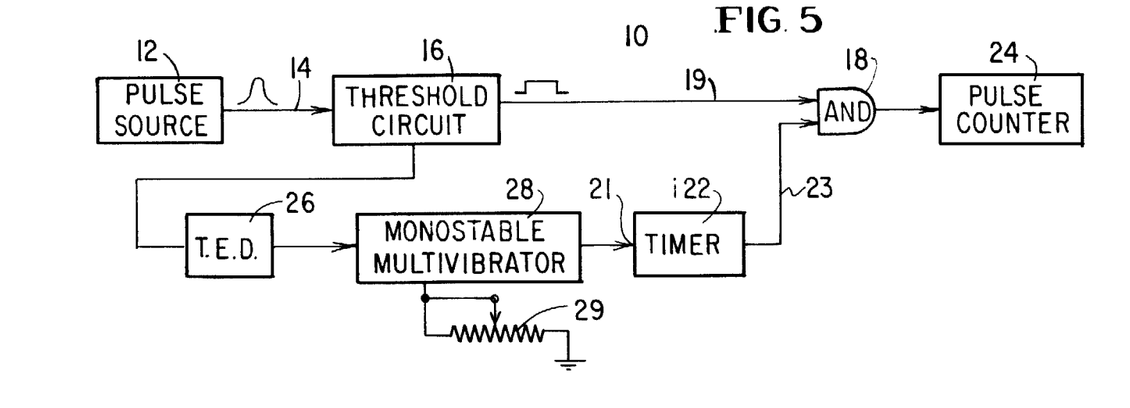
FIG. 5 is a block diagram of a modified form of the apparatus shown in FIG. 1.

Referring to FIG. 5, an apparatus is shown which provides a coincidence count correction in systems where substantially all particle pulses have the same pulse width indicating that the time period of cells within the scanning aperture is substantially constant. The circuit shown in FIG. 5 is substantially the same as is shown in FIG. 1 and operates in substantially the same manner so that it will not be described in detail. The connection to OR gate 20 and the OR gate 20 itself shown in FIG. 1 have been deleted in FIG. 5 and the output of monostable 28 is connected directly to timer 22. Trailing edge detector 26 and monostable 28 operate in the same manner as described with respect to FIG. 1 to directly inhibit timer 22 for a predetermined time period which is selectable by adjustment of potentiometer 29.

It should be understood that the apparatus shown in FIG. 5 performs all of the functions of the apparatus shown in FIG. 1. In the apparatus of FIG. 5, however, the function performed by the connection from threshold circuit 16 through OR gate 20, i.e., the pulse width correction corresponding to particle time in the aperture, has been incorporated into the operation of monostable 28 by proper selection of its time period. The pulse duration of monostable 28 is adjusted to represent the average duration in the scanning aperture of a blood cell being measured. It can be longer or shorter than the pulse width produced by passage of a particle. The only requirement on the duration of the pulse produced by monostable 28 is that the total time extension provided by inhibiting the timer 22 in response to each cell must be sufficient to allow additional cell counts totaling the coincidence error count. It should also be understood that the same modification to the apparatus in FIG. 1 made in FIG. 5 may also be made to the apparatus shown in FIG. 4.

Figure 6:
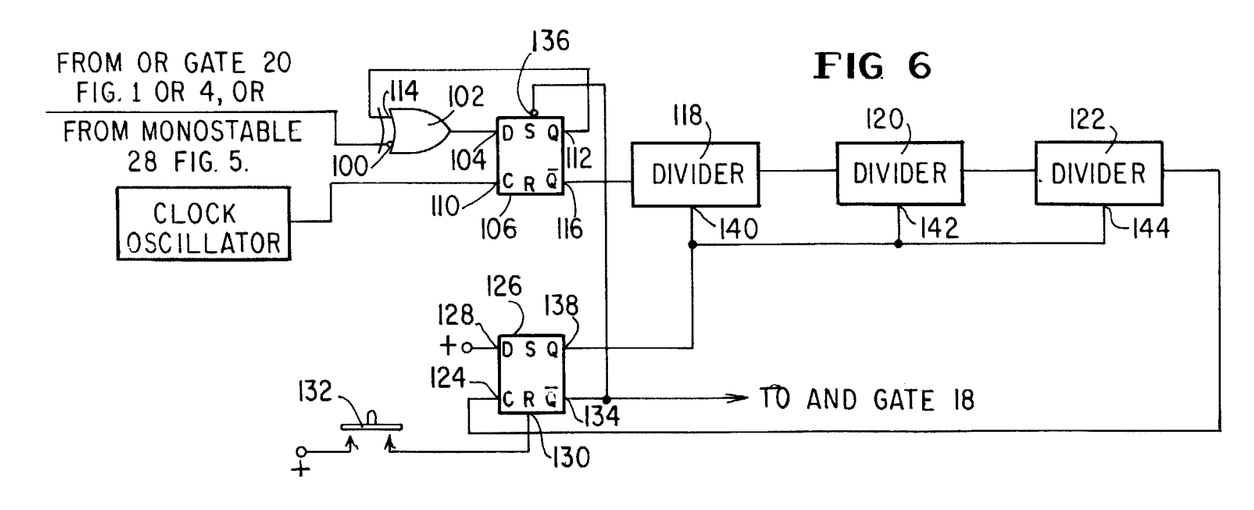
FIG. 6 is a schematic diagram of a portion of the apparatus shown in FIGS. 1, 4 and 5.

Referring now to FIG. 6, there is shown a schematic diagram of the timer 22 shown in FIGS. 1, 4 and 5. The pulses coupled from OR gate 20, or from monostable 28 as the case may be, are coupled to one input 100 of an exclusive OR (Ex OR) gate 102. The output of Ex OR gate 102 is coupled to input 104 of a bistable multivibrator 106 termed the gate bistable. Ex OR gate 102 and bistable 106 together can be considered to constitute a gate.

In the preferred embodiment, bistable 106 is a D type bistable and input 104 is the D input. A clock oscillator 108, which develops a one megahertz signal is coupled to input 110, the clock or C input of bistable 106. Output 112, the Q output of bistable 106 is coupled to a second input 114 of Ex OR gate 102, and output 116, the $\bar{Q}$ output of bistable 106 is coupled to the input of a divider circuit 118.

Divider circuit 118, although it is technically known as a divider, will count the pulses received and develop an output signal in response to a particular number of counts. In the embodiment shown, divider circuit 118 is a divide by $2^{14}$ circuit so that it will develop an output signal in response to each 16,384 pulses received at its input. The output of divider circuit 118 is coupled to a second divider circuit 120 which divides the signals received at its input by 10 and develops one output signal in response to each ten received input signals. The output of divider circuit 120 is coupled to the input of divider circuit 122 which is also a divide by 10 circuit. Divider circuits 118, 120 and 112 form what is known in the art as a ripple counter which counts the number of received pulses and develops an output pulse after a particular number of input pulses have been received.

The output of divider circuit 122 is coupled to input 124, the C input of a bistable multivibrator 126. Bistable 126 is termed the stop-start bistable. Input 128, the D input of bistable 126 is coupled to a positive potential, and input 130, the reset input, is coupled through a start switch 132 to positive potential. Output 134, the $\overline{Q}$ of bistable 126 is coupled to AND gate 18 in FIGS. 1, 4 and 5 and to the set or S input 136 of bistable 106. Output 138, the Q output of bistable 126, is coupled to the reset inputs 140, 142 and 144 of divider circuits 118, 120 and 122, respectively.

Operation of timer circuit 22 is initiated by depression of start switch 132. This couples the positive signal to stop-start bistable 126 causing it to change states and develop a high signal at output 134 and a low signal at output 138. The high signal developed at output 134 is coupled to one input of AND gate 18, thus partially enabling AND gate 18 as previously discussed. The high signal is also coupled to set input 136 of bistable 106 where the circle represents an inversion function. With a high signal present at input 136, bistable 106 is no longer inhibited and can operate in response to pulses at either input 104 or 110. The termination of the high signal at output 138 of bistable 126 terminates the reset of divider circuits 118, 120 and 122 allowing them to sequentially count in response to received pulses. Consequently, the presence of a low signal at output 138 allows divider circuits 118, 120 and 122 to count.

The pulses developed by clock oscillator 108 are coupled to input 110 of bistable 106. If bistable 106 is not inhibited, it will change states in response to each received clock pulse so that a 500 KHZ pulse train will be developed at output 116 of bistable 106. Divider circuits 118, 120 and 122 would add the pulses received from output 116 and would develop an output pulse at the output of divider circuit 120 at the end of a series of 3,276,800 pulses from clock oscillator 108. Converting this to a time base, if there were no interruptions or extensions of the total time period, timer circuit 22 in the preferred embodiment would operate for a time period of approximately 3.28 seconds. At the end of this time period the divider circuit 122 would develop an output signal which is coupled to input 124, the clock input of bistable 126. This output signal will cause bistable 126 again to change states and develop a high signal at output 138 and a low signal at output 134. The low signal at output 134 will inhibit AND gate 18 and bistable 106 and the high signal at output 138 will reset the divider circuits 118, 120 and 122 and inhibit further counting.

When operation of time circuit 22 is initiated and it is timing the predetermined interval, pulses from OR gate 20 in FIGS. 1 and 4, or from monostable 28 in FIG. 5 may be coupled to input 100 of exclusive OR gate 102. The circle shown at input 100 of exclusive OR gate 102 represents an inverter or inversion function so that the positive or high level inhibit signal from either OR gate 20 or monostable 28 will be inverted and will become a low signal at Ex OR gate 102 with a low signal received at input 100 of EX OR gate 102, the bistable 106 will be inhibited from changing state in response to clock pulses received at input 110. The inhibit function will be maintained during the presence of each pulse from either OR gate 20 or monostable 28 thus extending the predetermined counting period by inhibiting further counting. With the termination of each pulse bistable 106 will no longer be inhibited and will again change states in response to each clock pulse coupled to input 110. In the preferred embodiment it has been found that the total timing period can be extended to 4.0 seconds as a result of the pulses coupled to input 100 of Ex OR gate 102.

It is to be understood that the method for providing the above noted particle pulse count corrected is also contemplated as being within the scope of this invention. Although a number of embodiments of apparatus for providing error correction of a particle pulse count have been shown and described, it is to be understood that other modifications of the above described circuitry are capable of being made without departing from the spirit and scope of the invention as defined in the appended claims.

We claim:

1. A method for correcting a particle pulse count subject to coincidence error including the steps of:
    counting the particle pulses received for a predetermined period of time,
    increasing said predetermined period of time by a fixed time increment in response to each pulse, the fixed time increment being a function of coincidence error and therefore related to pulse width.

2. The method of claim 1 wherein the step of counting the particle pulses for a predetermined period of time includes the step of detecting particle pulses in excess of a first amplitude and counting said detected particle pulses.

3. A method for automatically correcting a particle pulse count subject to coincidence error including the steps of measuring a predetermined time period during which time period said received particle pulses are counted and inhibiting measurement of said predetermined time period by a fixed time increment in response to each received particle pulse said fixed time increment being related to the characteristics of the particle pulse received and therefore to the coincidence error.

4. An apparatus for automatically correcting a particle pulse count subject to coincidence error wherein the particle pulses are developed in response to passage of particles in a particulate system through a particle sensing device, said apparatus including in combination,
    timer means operative to count the particle pulses for a predetermined period of time, and
    control means coupled to said timer means and operative to increase said predetermined period of time by a time increment in response to each particle pulse, said control means including detection circuit means coupled to said particle sensing device and operative in response to each particle pulse to develop said control signal for a fixed duration, said fixed duration being selected such that it is related to the particle pulse characteristics and therefore to the coincidence error.

5. The apparatus of claim 4 further including detection means coupling said particle sensing device to said timer means and control means, said detection means operative in response to particle pulses in excess of a first amplitude to develop detection signals and couple said signals to said timer means and control means.

6. The apparatus of claim 4 wherein said timer means includes, counter means for counting said particle pulses, and a timer circuit coupled to said counter means for enabling said counter means to count said particle pulses for said predetermined period of time.

7. The apparatus of claim 6 wherein said timer circuit generates a timing signal for said predetermined time period, said counter means including gating means coupled to said particle sensing device and said timer circuit and operative in response to said timing signal and each particle pulse detected to develop a gating signal, and a counter circuit coupled to said gating means for counting each gating signal.

8. The apparatus of claim 7 wherein said gating means is an AND gate.

9. The apparatus of claim 4 wherein said detection circuit includes monostable means operative in response to each particle pulse to develop said fixed duration control signal said monostable means including means for selecting the period of said fixed duration.

10. The apparatus of claim 9 wherein said detection circuit includes a trailing edge detection circuit coupled to said particle sensing device and operative in response to the trailing edge of each of said particle pulses to develop a detection pulse, said monostable means being coupled to said trailing edge detection circuit and operative in response to each detection pulse to develop said control signal.

11. In a particle analyzer subject to coincidence error wherein particle pulses are developed in response to passage of particles in a particulate system through a sensing zone, the improvement comprising,
   detection means operative in response to receipt of particle pulses to develop detection signals having a duration equal to the period said particle pulses exceed a predetermined amplitude,
   timer means coupled to said detector means and operative to count said detection signals for a predetermined period of time, and
   control means coupled to said detection means and said timer means and operative to increase said predetermined period of time by a time increment in response to each detection signal, said time increment duration being related to a characteristic of said detection signal and therefore to coincidence error.

12. The apparatus of claim 11 wherein said control means is operative to increase said predetermined period of time by a fixed time increment in response to the termination of each detection signal.

13. The apparatus of claim 12 wherein said control means is further operative to increase said predetermined time period by a second time increment in response to the termination of each detection signal, said second time increment having a duration which is a function of the repetition rate of said particle pulses.

14. In a particle analyzer subject to coincidence error wherein particle pulses are developed in response to passage of particles in a particulate system through a sensing zone and wherein the coincidence error is a function of particle passage time the improvement comprising;
   detection means operative in response to receipt of particle pulses in excess of a predetermined amplitude to develop detection pulses,
   timer means coupled to said detection means and operative to count said detection signals for a predetermined period of time, and
   control means coupled to said detection means and said timer means and operative in response to each detection signal to increase said predetermined period of time by a fixed time increment, said time increment duration being a function of particle passage time and therefore of coincidence error.

15. An apparatus for automatically correcting a particle pulse count subject to coincidence error wherein the particle pulses are developed in response to passage of particles in a particulate system through a particle sensing device and wherein the coincidence error is related to particle passage time through said sensing device, said apparatus including in combination,
   timer means operative to count the particle pulses for a predetermined period of time, and
   control means coupled to said timer means and operative to increase said predetermined period of time by a fixed time increment in response to each particle pulse, said time increment duration being related to particle passage time and therefore to coincidence error.

16. The apparatus of claim 15 wherein said timer means include, counter means for counting said particle pulses, and a timer circuit coupled to said counter means for enabling said counter means to count said particle pulses for said predetermined period of time.

17. The apparatus of claim 16 wherein said control means include detection circuit means coupled to said particle sensing device and operative in response to each particle pulse to develop said control signal for a fixed duration, said fixed duration being selected such that it is related to the particle passage time and therefore to the coincidence error.

18. The apparatus of claim 17 wherein said timer circuit includes, a clock oscillator for developing clock pulses, gate means coupled to said clock oscillator and operative to pass said clock pulses therethrough, a counter circuit coupled to said gate means for counting a particular number of said clock pulses in said predetermined time period and for developing an enable signal during said counting for enabling said counter means, stop-start control means coupled to said gate means and counter circuit, said stop-start control means operative when disabled to inhibit passage of said clock pulses through said gate means, to inhibit counting by said counting circuit and to inhibit said enable signal, said stop-start circuit operative when enabled to become disabled in response to termination of said enable signal, said gate means being coupled to said control means and operative in response to said control signal to inhibit passage of said clock pulses through said gate means.

19. The apparatus of claim 18 wherein said stop-start control means include bistable means.

20. The apparatus of claim 17 wherein said detection circuit includes monostable means operative in response to each particle pulse to develop said fixed duration control signal said monostable means including means for selecting the period of said fixed duration.

21. The apparatus of claim 20 wherein said detection circuit includes a trailing edge detection circuit coupled to said particle sensing device and operative in response to the trailing edge of each of said particle pulses to develop a detection pulse, said monostable means being coupled to said trailing edge detection circuit and operative in response to each detection pulse to develop said control signal.

* * * * *